_(12)_ United States Patent
Yagou et al.

(10) Patent No.: US 6,897,350 B2
(45) Date of Patent: May 24, 2005

(54) BODY FLUID ABSORBENT PANEL FOR SANITARY WEARING ARTICLE

(75) Inventors: Toshiya Yagou, Kagawa-ken (JP); Kazuaki Onishi, Kagawa-ken (JP)

(73) Assignee: Uni-Charm Corporation, Ehime-ken (JP)

( * ) Notice: Subject to any disclaimer, the term of this patent is extended or adjusted under 35 U.S.C. 154(b) by 42 days.

(21) Appl. No.: 09/939,163

(22) Filed: Aug. 24, 2001

(65) Prior Publication Data

US 2002/0026168 A1 Feb. 28, 2002

(30) Foreign Application Priority Data

Aug. 25, 2000 (JP) .......................................... 2000-301206

(51) Int. Cl.$^7$ ................................................. A61F 13/15
(52) U.S. Cl. ...................................... 604/372; 604/378
(58) Field of Search ............................. 604/365–368, 604/370, 372, 378, 383; 442/327, 334, 340, 341, 345, 350, 366, 377, 349

(56) References Cited

U.S. PATENT DOCUMENTS

| | | | |
|---|---|---|---|
| 4,276,338 A | | 6/1981 | Ludwa et al. |
| 4,560,372 A | * | 12/1985 | Pieniak ........................ 604/366 |
| 4,704,112 A | | 11/1987 | Suzuki et al. |
| 4,710,185 A | * | 12/1987 | Sneyd et al. ................. 604/372 |
| 4,780,352 A | * | 10/1988 | Palumbo ...................... 428/138 |
| 5,478,335 A | * | 12/1995 | Colbert ........................ 604/366 |
| 5,490,846 A | * | 2/1996 | Ellis et al. ................. 428/304.4 |
| 5,536,264 A | * | 7/1996 | Hsueh et al. ................ 604/365 |
| 5,567,501 A | * | 10/1996 | Srinivasan et al. .......... 428/137 |
| 5,817,394 A | | 10/1998 | Alikhan et al. |
| 5,885,267 A | * | 3/1999 | Mishima et al. ............. 604/378 |
| 5,928,210 A | * | 7/1999 | Ouellette et al. ............ 428/323 |
| 6,015,936 A | * | 1/2000 | Takai et al. .................. 604/358 |
| 6,140,550 A | * | 10/2000 | Beihoffer et al. ............ 604/365 |
| 6,274,218 B1 | * | 8/2001 | Shimizu ....................... 428/137 |
| 6,395,957 B1 | * | 5/2002 | Chen et al. .................. 604/381 |

FOREIGN PATENT DOCUMENTS

| | | |
|---|---|---|
| EP | 0 545 423 | 8/1997 |
| EP | 0 815 819 | 1/1998 |
| EP | 0 953 324 | 11/1999 |
| EP | 1 138 301 | 10/2001 |
| JP | 5-253259 | 10/1993 |
| WO | WO 00/35503 | 6/2000 |

\* cited by examiner

_Primary Examiner_—Larry I. Schwartz
(74) _Attorney, Agent, or Firm_—Butzel Long

(57) ABSTRACT

A body fluid absorbent panel including openings and a barrier which comprises, in turn, a shape keeping layer formed with a plurality of thermoplastic synthetic resin fibers and a body fluid retaining layer formed with a plurality of thermoplastic synthetic fibers mixed with an absorbent material, wherein the synthetic resin fibers are hot welded together at contact points of these fibers in the shape keeping layer as well as in the body fluid retaining layer and the synthetic resin fibers of these layers are hot welded together at contact points of these fibers along an interface of the shape keeping layer and the body fluid absorbent layer.

13 Claims, 4 Drawing Sheets

BODY FLUID ABSORBENT PANEL FOR SANITARY WEARING ARTICLE

BACKGROUND OF THE INVENTION

This invention relates to a body fluid absorbent panel used for a sanitary wearing article such as a disposable diaper, a sanitary napkin or a liquid-absorbent pad for an incontinent patient.

Japanese Patent Application Publication No. 1993-253259A describes a disposable diaper including between a liquid-pervious topsheet and a liquid-impervious backsheet a panel serving to absorb and to hold excretion discharged on this diaper wherein the panel has a plurality of openings extending through the panel in a direction of its thick direction. In this diaper of prior art, excretion discharged thereon is received by the openings and then absorbed by the panel. This arrangement is claimed to be effective to avoid an anxiety that a certain amount of excretion might stay on the topsheet. The Publication describes an embodiment of the panel comprising a mixture of thermoplastic synthetic resin fibers, fluff pulp and high absorption polymer grains.

The Publication describes intertwinement of the synthetic resin fibers in the panel but no description is found therein that the synthetic resin fibers are hot welded together at contact points thereof. Accordingly, it is impossible for this panel of prior art to restrict a relative movement among these synthetic resin fibers. Consequently, the panel is readily collapsed under a pressure exerted thereon in a direction of its thickness and unable to restore a desired thickness from the collapsed state. Particularly because this panel has a plurality of openings, a resistance against the pressure exerted thereon in the direction of its thickness is correspondingly lower and the panel may be readily collapsed even under a slight pressure exerted thereon.

In addition, this panel of prior art is arranged so that the high absorption polymer grains are merely held in fiber interstices of the synthetic resin fibers and the fluff pulp. As a result, the polymer grains may be disengaged from the fiber interstices of the synthetic resin fibers and the fluff pulp and fall off from the panel as the panel is collapsed.

SUMMARY OF THE INVENTION

It is an object to provide a body fluid absorbent panel adapted to resist against collapse under a pressure exerted thereon in a thickness direction and to restore a desired thickness dimension even if more or less collapsed.

According to this invention, there is provided a body fluid absorbent panel used for a sanitary wearing article made of a fibrous web having a compression resilience, the fibrous web having a plurality of openings extending therethrough in a direction of its thickness and a barriers surrounding the openings.

According to this invention the barrier comprises a shape keeping layer formed with a plurality of thermoplastic synthetic resin fibers and a body fluid retaining layer placed upon one of an upper surface and a lower surface of the shape keeping layer and formed with a plurality of thermoplastic resin fibers mixed with absorbent material, and the synthetic resin fibers are hot welded together at contact points of these fibers in the shape keeping layer and in the body fluid retaining layer and, along an interface of the shape keeping layer and the body fluid regaining layer, the synthetic resin fibers of these layers are hot welded together at contact points of these fibers. As used herein, the term "compression resilience" refers to a property that a fibrous web can be compressed and restored in a direction of its thickness as resiliently as rubber or soft urethane foam.

This invention includes embodiments as follow:

(1) The absorbent material comprises hot weldable high absorption polymer grains and/or a plurality of liquid-absorbent fibers made of high absorption polymer so that the synthetic resin fibers and the polymer particles are hot welded together at contact points thereof in the body fluid retaining layer and wherein the synthetic resin fibers of the shape keeping layer and the polymer particles of the body fluid retaining layer are hot welded together at contact points thereof along the interface of the shape keeping layer and the body fluid retaining layer.

(2) The barrier comprises a plurality of first barriers extending in parallel to and spaced apart from one another in a first direction and a plurality of second barriers extending in parallel to and spaced apart from one another in a second direction intersecting the first barrier and each of the openings is defined by a pair of the adjacent first barriers and a pair of the adjacent second barriers intersecting the pair of the adjacent first barriers.

(3) At least the two panels are placed upon each other in the direction of thickness so that each of the openings formed in an upper one of the panels is divided by the barrier formed in the panel immediately underlying the upper one of the panels at least in two sections.

(4) An open area ratio of the openings to the panel is in a range of 20–80% and a total area of the openings is in a range of 10~1600 mm$^2$ and wherein a total area of the openings in the upper panel and a total area of the openings in the panel immediately underlying the upper panel are in a relationship of the upper panel ≦ the panel immediately underlying the upper panel.

(5) A compression resilience of the barrier is in a range of (a thickness under a load of 35 g/cm$^2$)÷(a thickness under a load of 2 g/cm$^2$)×100=20~80%.

(6) A ratio between the shape keeping layer and the body fluid retaining layer with respect to a dimension the barrier as measured in its thickness direction is in a relationship of (shape keeping layer) 6:4 (body fluid retaining layer)~(shape keeping layer) 8:2 (body fluid retaining layer).

(7) The body fluid absorbent layer contains a plurality of cellulose fibers.

(8) A mat-like liquid-absorbent core substantially without any openings is provided on a lower surface of a lowermost one of the panels.

DETAILED DESCRIPTION OF THE PREFERRED EMBODIMENTS

Details of a body fluid absorbent panel for sanitary wearing article according to this invention will be more fully understood from the description given hereunder with reference to the accompanying drawings.

Figure 1:
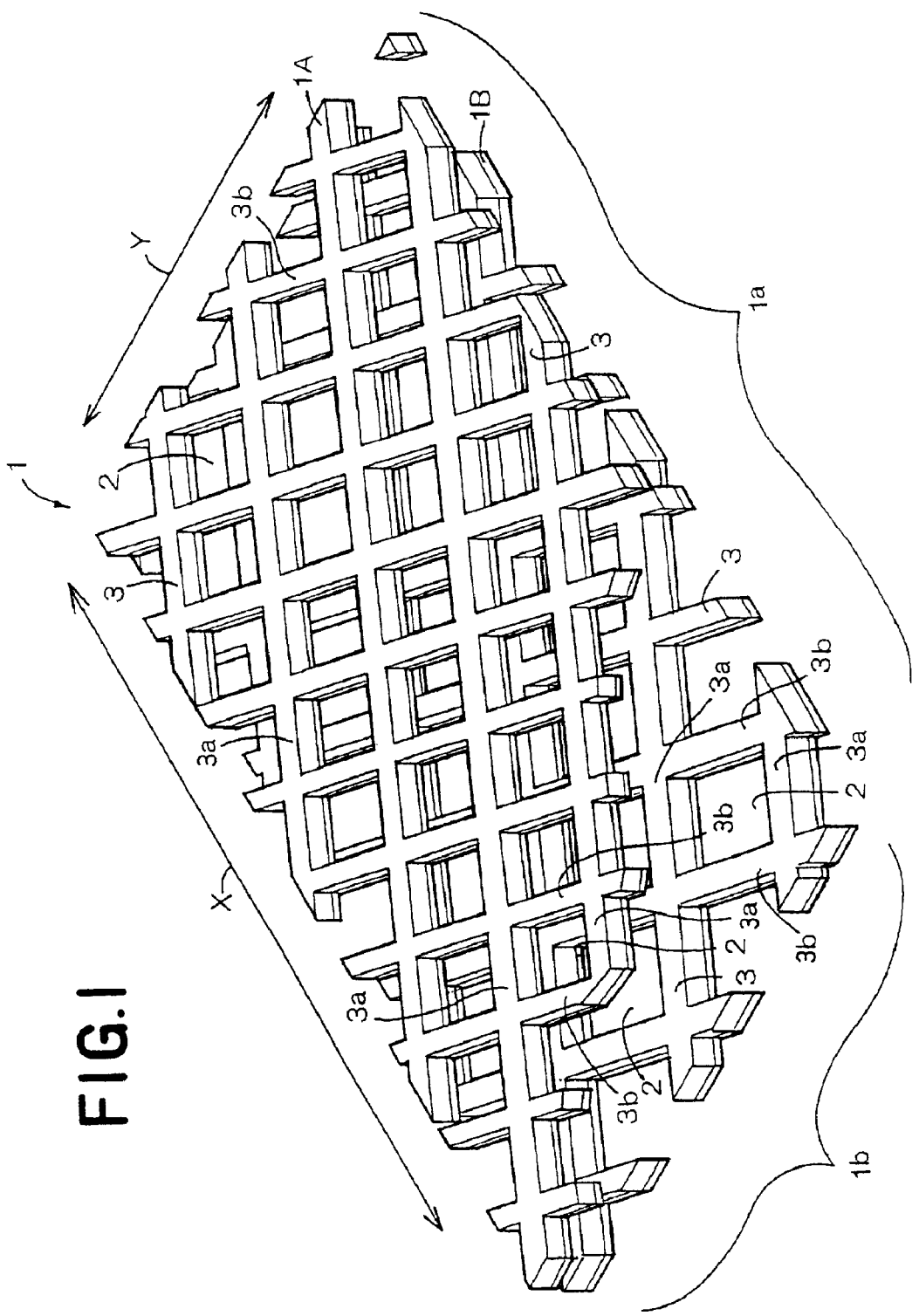
FIG. 1 is a perspective view showing a body fluid absorbent panel as partially broken away.
Figure 2:
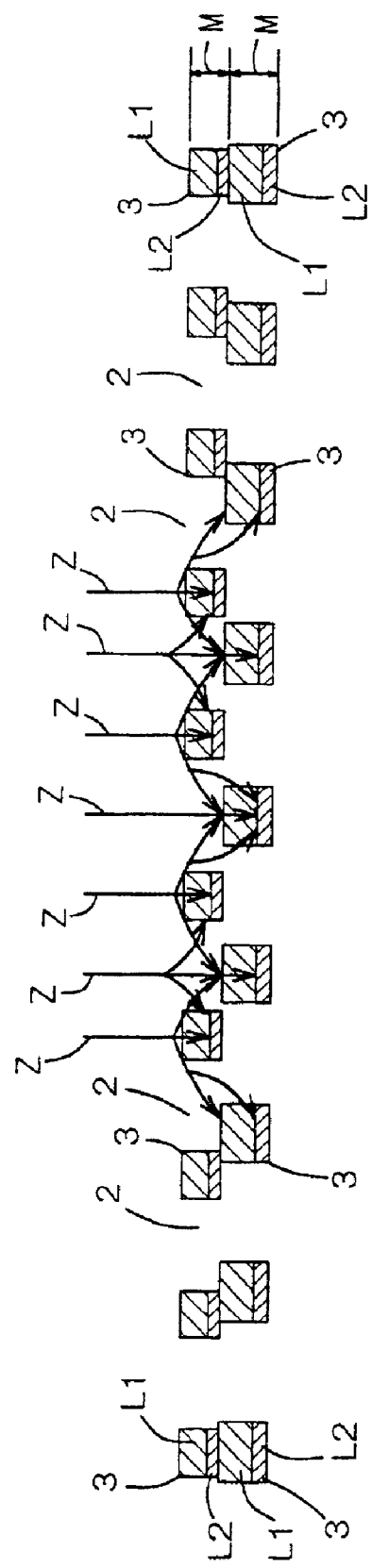
FIG. 2 is a schematic diagram of the panel illustrating permeation, spreading and absorption of excretion therein.

FIG. 1 is a perspective view showing a body fluid absorbent panel 1 as partially broken away and FIG. 2 is a schematic diagram of the panel 1 illustrating permeation, spreading and absorption of excretion therein. A longitudinal direction is indicated by an arrow X and a transverse direction is indicated by an arrow Y in FIG. 1 and a flow of excretion is indicated by an arrow Z in FIG. 2.

The body fluid absorbent panel 1 is formed with a fibrous web having a compression resilience and comprises transversely opposite side edge portions 1a extending in the longitudinal direction and longitudinally opposite end portions 1b extending in the transverse direction.

The panel 1 consists of separate first and second panels 1A, 1B placed upon each other in its thickness direction. The first and second panels 1A, 1B have a plurality of openings 2 extending through these panels 1A, 1B in a thickness direction thereof and a barrier 3 surrounding these openings 2. The barrier 3 comprises a plurality of first barriers 3a and a plurality of second barriers 3b. The first barriers 3a extending in parallel to and spaced apart from one another obliquely with respect to the transversely opposite side edge portions 1a as well as to the longitudinally opposite end portions 1b of the panel 1 and the second barriers 3b also obliquely extend in parallel to and spaced apart from one another so as to intersect the first barriers 3a. In the first and second panels 1A, 1B, the first barriers 3a and the second barriers 3b are bonded together at overlapping portions thereof.

Each of the openings 2 is defined by a pair of the adjacent first barriers 3a and a pair of the adjacent second barriers 3b intersecting said pair of the adjacent first barriers 3a. In the panel 1, the openings 2 of the first panel 1A are out of coincidence with the openings 2 of the second panel 1B so that each of the openings 2 in the first panel 1A may be divided by the first and second barriers 3a, 3b of the second panel 1B in a plurality of sections, including at least in two sections. In the panel 1, a total area occupied by the openings 2 in the first panel 1A and a total area occupied by the openings 2 in the second panel 1B are in a relationship of the first panel<the second panel.

The barrier 3 comprises a shape keeping layer L1 formed with a plurality of thermoplastic synthetic resin fibers and a body fluid retaining layer L2 formed with a plurality of thermoplastic synthetic resin fibers mixed with absorbent material and fluff pulp. In the barrier 3, the body fluid retaining layer L2 underlies the shape keeping layer L1. The absorbent material comprises hot weldable high absorption polymer particles and a plurality of liquid-absorbent fibers made of high absorption polymer.

In the shape keeping layer L1, the synthetic resin fibers are mechanically entangled with or placed one upon another and hot welded together at contact points thereof. In the body fluid retaining layer L2, on the other hand, the synthetic resin fibers, the fluff pulp and the liquid-absorbent fibers are mechanically entangled with or placed upon one another wherein the synthetic resin fibers are hot welded together at contact points of these fibers. In the body fluid retaining layer L2, the polymer particles are held interstices defined by the synthetic resin fibers, the fluff pulp and the liquid-absorbent fibers wherein the synthetic resin fibers and the polymer particles are hot welded together at contact points thereof.

Along a contact surface between the shape keeping layer L1 and the body fluid retaining layer L2, the synthetic resin fibers of these layers L1, L2 are hot welded at contact points thereof while the synthetic resin fibers of the shape keeping layer L1 and the polymer particles of the body fluid retaining layer L2 are hot welded at contact points thereof.

In the barrier 3, the synthetic resin fibers are hot welded together only at the contact points thereof in the shape keeping layer L1 as well as in the body fluid retaining layer L2. Accordingly, the synthetic resin fibers restrict themselves against any relative movement of these fibers so that the layers L1, L2 may be prevented from being collapsed. Even if these layers L1, L2 are more or less collapsed under a pressure exerted on these layers L1, L2 in their thickness directions, the layers L1, L2 can restore their initial thickness.

The shape keeping layer L1 particularly comprising the synthetic resin fibers presents a higher resistance to the pressure than the body fluid retaining layer L2 and has a compression resilience. In this manner, a resistance of the barrier 3 against the pressure as well as a restorative elasticity after compression of the barrier 3 can be reliably achieved. In the body fluid retaining layer L2, on the other hand, it is less likely that the polymer particles might fall off from the body fluid retaining layer L2 even if the barrier 3 is collapsed since the synthetic resin fibers and the polymer particles are hot welded at the contact points thereof.

As illustrated in FIG. 2, excretion permeates into the shape keeping layer L1 through top and side surfaces of the barrier 3 in the first panel 1A and simultaneously is absorbed in the body fluid retaining layer L2 through the side surface of the barrier 3 and held therein. The amount of excretion has reached the second panel 1B without absorbed by the first panel 1A permeates into the shape keeping layer L1 through top and side surfaces of the barrier 3 in the second panel 1B and simultaneously is absorbed in the body fluid retaining layer L2 through the side surface of the barrier 3 and held therein. The amount of excretion having permeated into the shape keeping layer L1 of the barrier 3 is transferred from the shape keeping layer L1 to the body fluid retaining layer L2 and held therein.

In the panel 1, the amount of excretion being absorbed in the barrier 3 in the first and second panels 1A, 1B is divided by the barrier 3 in the panels 1A, 1B into a plurality of flows. In the panel 1, the flow of excretion can be quickly spread from the first panel 1A toward the second panel 1B. On the other hand, transfer of excretion from the second panel 1B to the first panel 1A can be obstructed.

An open area ratio of the openings 2 to the panel 1 is in a range of 20~80% and a total area of the openings 2 is in a range of 10~1600 mm$^2$. The open area ratio referred to herein is a ratio of the total area of the openings 2 to the total area of the panel 1. In the case of the open area ratio less than 20% and the total area of the openings 2 less than 10 mm$^2$, it would be impossible for the openings 2 to receive the whole amount of excretion and an excessive amount of excretion may stay on the top surface of the first panel 1A. In the case of the open area ratio exceeding 80% and the total area of the openings 2 exceeding 1600 mm$^2$, the resistance of the barrier 3 against a pressure exerted thereon would be significantly decreased and the barrier 3 may readily be collapsed under a slight pressure.

In the panel 1, the barrier 3 has a compression resilience in a range of (thickness under a load of 35 g/cm$^2$)÷(thickness under a load of 2 g/cm$^2$)×100 =20~80%. With the compression resilience less than 20%, the barrier 3 could not restore its initial thickness once the barrier 3 has been collapsed, i.e., the initial volume of the barrier 3 would be substantially reduced and consequently an absorbing capacity of the barrier 3 for excretion would remarkably decrease with respect to the absorbing capacity achieved before the barrier 3 is collapsed. With the compression resilience exceeding 80%, on the contrary, the barrier 3 would become too stiff to offer a flexibility desired for the sanitary wearing article.

In the panel 1, a ratio between the shape keeping layer L1 and the body fluid retaining layer L2 with respect to a dimension M of the barrier 3 as measured in its thickness direction is preferably in a relationship of (shape keeping layer) 6:4 (body fluid retaining layer)~(shape keeping layer) 8:2 (body fluid retaining layer). With the shape keeping layer L1 exceeding 80%, a percentage of the body fluid layer L2 retaining is lowered and, therefore, its absorbing capacity for excretion in the barrier 3 would be correspondingly declined. With the shape keeping layer L1 less than 60%, its volume would be insufficient to ensure that the barrier 3 properly resist against a pressure exerted thereon. It should be understood that the dimension M of the barrier 3 as measured in its thickness dimension is preferably in a range of 5~50 mm, more preferably in a range of 10~30 mm.

Process for making the panel exemplarily comprises the steps of discharging and dispersing thermoplastic synthetic resin fibers, fluff pulp, hot weldable high absorption polymer particles and liquid-absorbent fibers in the air, accumulating them on a movable conveyor provided on its top with a plurality of convex pins shaped and arranged to define the openings to form the body fluid retaining layer, discharging and dispersing thermoplastic synthetic resin fibers in the air, accumulating these thermoplastic synthetic resin fibers on the body fluid retaining layer to form the shape keeping layer, and blowing hot air against the shape keeping layer placed upon the body fluid retaining layer on the movable conveyor so that the synthetic resin fibers are hot welded together and, at the same time, the synthetic resin fibers are hot welded with the hot weldable high absorption polymer particles to form the panel.

The synthetic resin fibers used to implement this invention may be selected from a group including fibers made of a polyolefin such as a polypropylene or a polyethylene, fibers made of a polyester such as a polyethylene terephthalate or a polybutylene terephthalate, fibers made of a polyamide such as a nylon 66 or a nylon 6, or acryl fibers. It is also possible to use core-sheath-type conjugated fibers or side-by-side-type conjugated fibers of a polyethylene/a polypropylene or a polyester as said synthetic resin fibers. The synthetic resin fibers are preferably treated to make them hydrophilic. The body fluid retaining layer may contain, in addition to the fluff pulp, cellulose-based fibers such as rayon or acetate fibers.

The panel may comprise three or more layers so far as each of the openings in the upper layer of panel is divided by the barrier in the layer of panel immediately underlying the upper layer of panel at least in two sections. In this case, it is preferable that the open area of the openings in each layer of panel is progressively reduced from the lowermost layer of panel toward the uppermost layer of panel. The panel may also comprise a single layer. An alternative arrangement is also possible in which the body fluid retaining layer is placed upon the upper surface of the shape keeping layer. The openings in the panel are not limited to the square openings as illustrated but may be of the other shape such as a circular, oval, rectangular or triangular shape.

Figure 3:
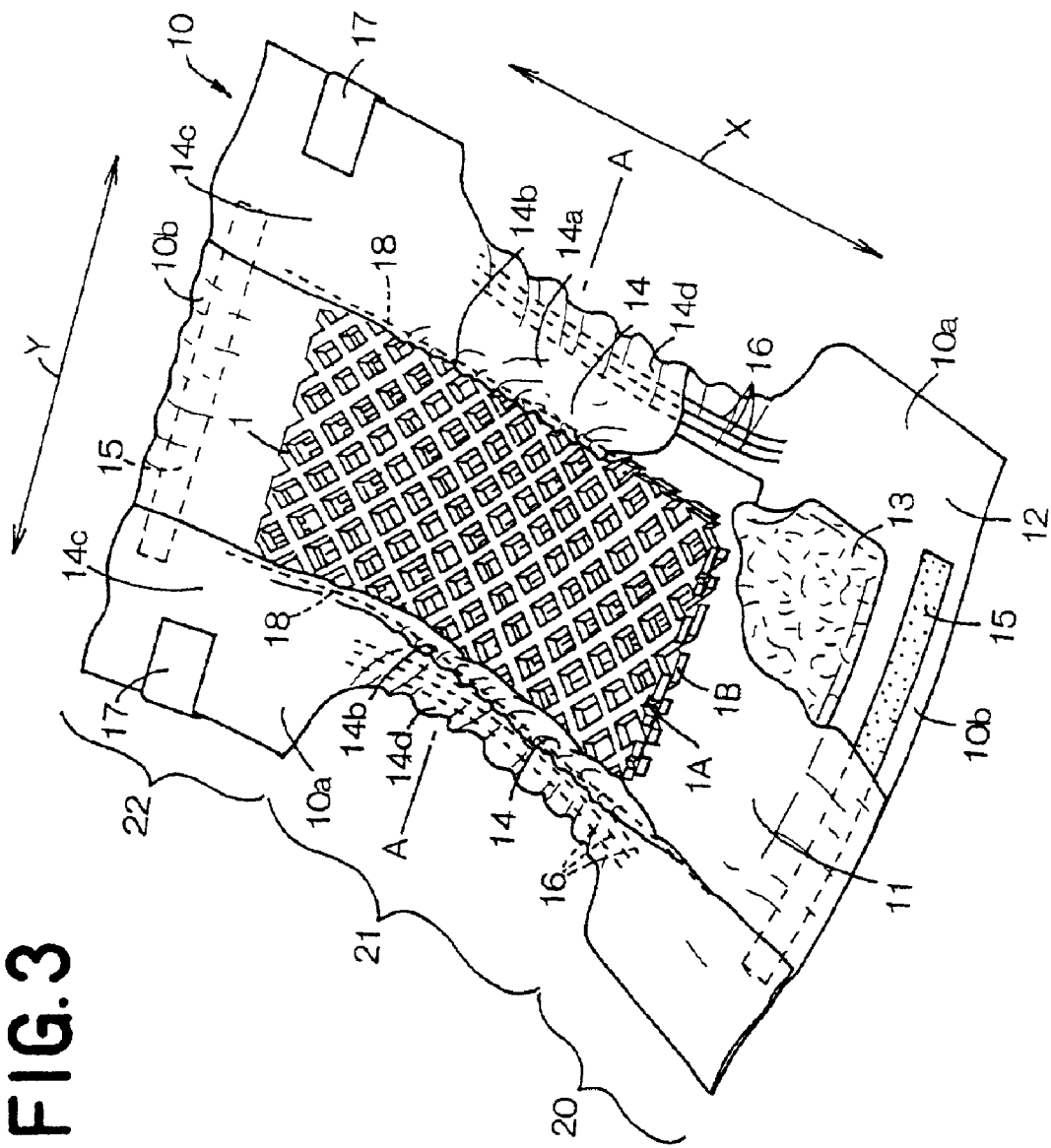
FIG. 3 is a perspective view showing the disposable diaper using the panel of FIG. 1 as partially broken away.
Figure 4:
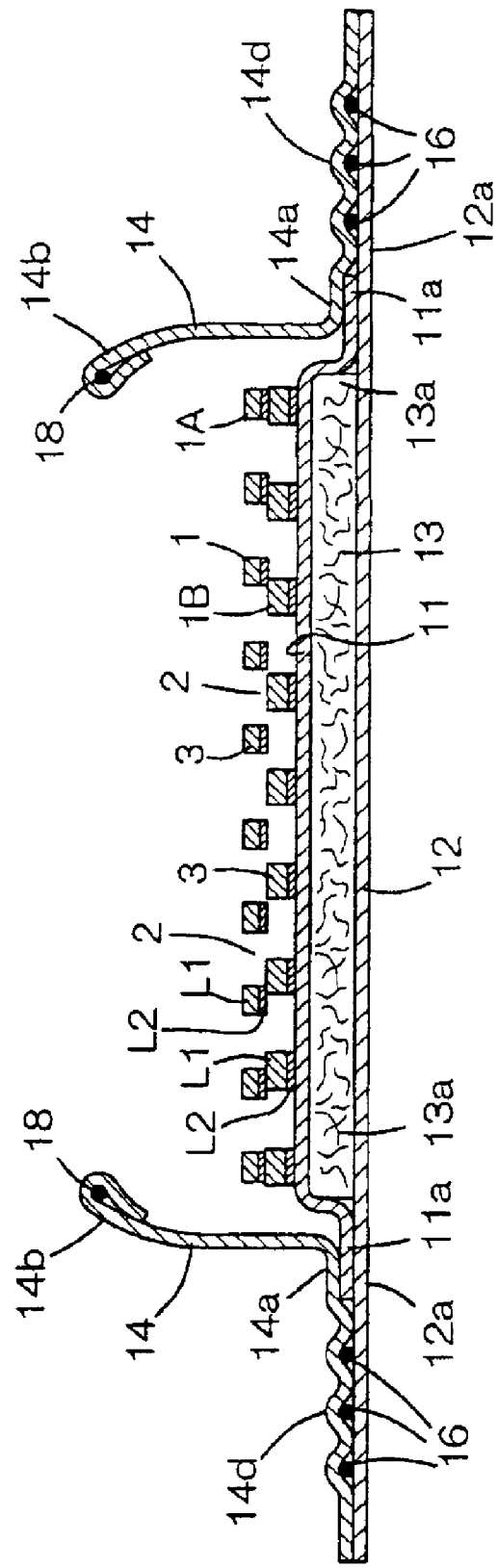
FIG. 4 is a sectional view taken along a line A—A in FIG. 3.

FIG. 3 is a perspective view showing the disposable diaper 10 using the panel 1 of FIG. 1 as partially broken away and FIG. 4 is a sectional view taken along a line A—A in FIG. 3. In FIG. 3, a longitudinal direction is indicated by an arrow X and a transverse direction is indicated by an arrow Y. The diaper 10 basically comprises a liquid-pervious topsheet 11, liquid-impervious backsheet 12, a liquid-absorbent core 13 substantially without openings and disposed between the two sheets 11, 12 and the panel 1.

The diaper 10 is composed, in the longitudinal direction, of a front waist region 20, a rear waist region 22 and a crotch region 21 extending between the front and rear waist regions 20, 22. The diaper 10 is contoured by longitudinally opposite end portions 10b extending in the transverse direction and transversely opposite side edge portions 10a extending in the longitudinal direction so as to describe circular arcs which are concave inwardly of the diaper 10 in the crotch region 21. The diaper 10 further comprises a pair of leak-barrier sheets 14 attached to the transversely opposite side edge portions 10a and extending in the longitudinal direction.

The core 13 is disposed between the top- and backsheets 11, 12 and entirely covered with and bonded to tissue paper (not shown). The core 13 is bonded to at least one of the top- and backsheets 11, 12 with said tissue paper therebetween. The panel 1 lies above the core 13 and a bottom surface of the second panel 1B is bonded to the topsheet 11.

A pair of film-like elastic members 15 extend in the transverse direction between the top- and backsheets 11, 12 along the longitudinally opposite end portions 10b of the diaper 10 and are bonded under tension to at least one of said top- and backsheets 11, 12. These elastic members 15 are associated with a waist-opening of the diaper 10. Similarly, a pair of elastic members 16 each comprising a plurality of elastic elements extend between the top- and backsheets 11, 12 in the longitudinal direction along the transversely opposite side edge portions 10a of the diaper 10 and are bonded under tension to at least one of said top- and backsheets 11, 12. These elastic members 16 are associated with respective leg-openings. A pair of tape fasteners 17 have respective proximal end portions attached to the transversely opposite side edge portions 10a of the diaper 10 in its rear waist region 22 and extend inward in the transverse direction, respectively. In the front waist region 20, a rectangular target tape strip (not shown) is attached to the outer surface of the backsheet 12 on which the tape fasteners 17 are anchored.

The leak-proof sheets 14 respectively comprise fixed side edge portions 14a extending immediately outside transversely opposite side edges 13a of the core 13 in the longitudinal direction and bonded to the topsheet 11, free side edge portions 14b lying in the crotch region 21 and extending inward in the transverse direction of the diaper 10 and normally biased to rise on the topsheet 11, and longitudinally opposite end portions 14c collapsed inward in the transverse direction of the diaper 10 and bonded to the topsheet 11 in such collapsed state. The leak-barrier sheets 14 further comprise outer side portions 14d extending outward laterally from the respective fixed side edge portions 14a. Elastic members 18 extending in the longitudinal direction are bonded under tension to the respective free side edge portions 14b. These elastic members 18 are covered with portions of the respective free side edge portions 14b.

Referring to FIG. 3, the diaper 10 is curved in its longitudinal direction with its inner surface inside and a plurality of gathers are formed along the transversely opposite side edge portions 10a as well as the longitudinally opposite end portions 10b of the diaper 10 and along the free side edge portions 14b of the respective leak-barrier sheets 14 as the elastic members 15, 16, 18 contract. A waist-opening and a pair of leg-openings (not shown) are defined as the tape fasteners 17 are anchored on the target tape strip by means of pressure-sensitive adhesive applied on the inner surfaces of the tape fasteners' free end portions.

Transversely opposite side portions 11a of the topsheet 11 extend outward slightly beyond the transversely opposite side edges 13a of the core 13 in the transverse direction and transversely opposite side portions 12a of the backsheet 12 as well as outer side portions 14d of the respective leak-proof sheets 14 extend outward from the opposite side portions 11a of the topsheet 11 in the transverse direction of the diaper 10. The opposite side portions 11a are respectively disposed between the side portions 12a and the outer side portions 14d and bonded to at least one of these portions 12a, 14d. The side portions 12a and the outer side portions 14d are put flat and bonded together. The elastic members 16 associated with the leg-openings are respectively disposed between the side portions 12a and the outer side portion 14d and bonded to at least one of these portions 12a, 14d.

In the longitudinally opposite end portions 10b of the diaper 10, portions of the top- and backsheets 11, 12 extending outward beyond longitudinally opposite ends of the core 13 in the longitudinal direction are put flat and bonded together.

Excretion discharged on the diaper 10 has its flow direction divided by the barrier 3 in the first and second panels 1A, 1B as the excretion is absorbed into the barrier 3 of these first and second panels 1A, 1B. Excretion quickly spreads from the first panel 1A toward the second panel 1B. An amount of excretion which has not been absorbed by the first and second panels 1A, 1B permeates the topsheet 11 into the core 13.

The topsheet 11 may be formed from a liquid-pervious sheet such as a nonwoven fabric or a porous plastic film, preferably with a liquid-pervious hydrophilic sheet. The backsheet 12 and the leak-proof sheets 14 may be formed from a hydrophobic nonwoven fabric, a liquid-impervious plastic film or a laminated sheet of a hydrophobic nonwoven fabric and a plastic film, preferably with a breathable but liquid-impervious sheet. It is also possible to form the backsheet and the leak-barrier sheets using composite nonwoven fabric consisting of a melt blown nonwoven fabric having a high water-resistance and two layers of a spun bond nonwoven fabric having high strength and flexibility sandwiching the melt blown nonwoven fabric.

The nonwoven fabric may be selected from a group including spun lace-, needle punch-, melt blown-, thermal bond-, spun bond-, chemical bond- and air through-nonwoven fabrics. Component fiber of the nonwoven fabric may be selected from a group including polyolefin-, polyester- and polyamide-based fibers and polyethylene/polypropylene or polyethylene/polyester core-sheath type conjugated fiber and side-by-side-type conjugated fiber.

The core 13 is a mixture of fluff pulp, high absorption polymer grains and thermoplastic synthetic resin fiber compressed to a desired thickness.

Bonding of the top- and backsheets 11, 12 to each other, bonding the core 13, the panel 1 and the leak-barrier sheets 14 to the top- and backsheets 11, 12 as well as attaching of the elastic member 15, 16, 18 may be carried out using a suitable adhesive agent such as a hot melt adhesive agent or a technique of welding such as a sonic sealing or a heat-sealing.

The panel 1 can be used not only in the disposable diaper but also in a sanitary napkin and a liquid-absorbent pad for incontinent patient.

According to the body fluid absorbent panel of the present invention, the barrier comprises the shape keeping layer in which the synthetic resin fibers are hot welded together at contact points of these fibers and the body fluid retaining layer in which the synthetic resin fibers are hot welded together at contact points of these fibers. This unique arrangement ensures the synthetic resin fibers to restrict themselves against any relative movement of these fibers so that the layers may be prevented from being collapsed. Even when these layers are more or less collapsed under a pressure exerted thereon in their thickness directions, the layers can restore their initial thickness. If the panel has not an adequate compression modulus to restore a desired thickness dimension after it has been collapsed, the volume of the barrier would be unacceptably reduced and its absorbing capacity for body fluids such as loose passage or menstrual discharge would be correspondingly reduced. The panel according to this invention effectively solves this problem by the unique construction of the barrier which is not readily collapsed and, even when it has been more or less collapsed, able to restore a sufficient thickness dimension to maintain a desired absorbing capacity for body fluids.

With the panel comprising two or more panel layers, the flow of body fluids is divided by the barrier so that the body fluids may quickly spread from the upper panel toward the lower panel. In other words, the entire panel can be efficiently used. With the panel comprising two or more panel layers, the area of the openings may be dimensioned to be progressively reduced from the lower panel toward the upper panel to avoid an anxiety that the body fluids might flow back from the lower panel toward the upper panel.

The panel is suitable for use in the sanitary wearing article such as a disposable diaper, a sanitary napkin or a liquid-absorbent pad for incontinent patient.

What is claimed is:

1. A body fluid absorbent panel for a sanitary wearing article comprising a fibrous web having a compression resilience, said fibrous web comprising a plurality of openings extending therethrough in a direction of a thickness of the fibrous web, and barriers surrounding and defining said openings, said barriers comprising a shape holding layer formed from a plurality of thermoplastic synthetic resin fibers that are hot welded together at contact points between the thermoplastic synthetic resin fibers so as to resist collapsing under pressure and a body fluid retaining layer placed upon one of an upper surface and a lower surface of said shape holding layer and formed from a plurality of thermoplastic synthetic resin fibers which are mixed with an absorbent material and are hot welded together at contact points between the thermoplastic synthetic resin fibers so as to resist collapsing under pressure, said shape holding layer and said body fluid retaining layers having surface pattern configurations defined by the barriers and exclusive of said openings which surface pattern configurations are substantially coextensive, said thermoplastic synthetic resin fibers of said shape holding layer being hot welded together at contact points thereof in said shape holding layer, said thermoplastic synthetic resin fibers of said body fluid retaining layer being hot welded together at contact points thereof in said body fluid retaining layer, and said thermoplastic synthetic resin fibers of said shape holding layer and said thermoplastic synthetic resin fibers of said body fluid retaining layer being hot welded to each other along an interface at contact points of said shape holding layer and said body fluid retaining layer.

2. The body fluid absorbent panel according to claim 1, wherein said absorbent material comprises a hot weldable high absorbent polymer component in the form of at least one of high absorption polymer particles and a plurality of liquid-absorbent fibers made of high absorption polymer, said thermoplastic synthetic resin fibers of said body fluid retaining layer and said high absorbent polymer component being hot welded together at contact points thereof in said body fluid retaining layer and said synthetic resin fibers of said shape holding layer and said high absorbent polymer component of said body fluid retaining layer being hot welded together at contact points thereof along said interface of said shape holding layer and said body fluid retaining layer.

3. The body fluid absorbent panel according to claim 1, wherein said barriers comprises a plurality of first barriers extending in parallel to and spaced apart from one another in a first direction and a plurality of second barriers extending in parallel to and spaced apart from one another in a second direction intersecting said first barriers and each of the openings is defined by a pair of adjacent first barriers and a pair of adjacent second barriers intersecting a pair of adjacent first barriers.

4. The body fluid absorbent panel according to claim 1, comprising at least two of said panels which are placed upon each other in a thickness direction so that openings formed in an upper one of said two panels are divided by at least in two sections by barriers formed in a panel immediately underlying said upper one of said two panels.

5. The body fluid absorbent panel according to claim 1, wherein an open area ratio of said openings to said panel is in a range of from about 20 to about 80% and a total area of said openings is in a range of from about 10 to about 1600 $mm_2$.

6. The body fluid absorbent panel according to claim 1, wherein a compression resilience of said barriers is in a range of from about 20 to about 80%.

7. The body fluid absorbent panel according to claim 1, wherein a ratio between said shape holding layer and said body fluid retaining layer with respect to a dimension of said barriers as measured in its thickness direction is in a range of 6:4 to 8:2.

8. The body fluid absorbent panel according to claim 1, wherein the body fluid absorbent layer contains a plurality of cellulose fibers.

9. The body fluid absorbent panel according to claim 1, wherein a mat-like liquid-absorbent core substantially without any openings is provided on a lower surface of said panel.

10. The body fluid absorbent panel according to claim 4, wherein an open area ratio of said openings to said panel is in a range of from about 20 to about 80% and a total area of said openings is in a range of from about 10 to about 1600 $mm^2$ and wherein a total area of said openings in said upper panel are less than or equal to a total area of said openings in the panel immediately underlying said upper panel.

11. The body fluid absorbent panel according to claim 1, further comprising a lower surface that is a mat-like liquid-absorbent core substantially without any openings.

12. The body fluid absorbent panel according to claim 1, wherein said shape holding layer comprises a liquid-permeable material.

13. A body fluid absorbent panel for a sanitary wearing article comprising a fibrous web having a compression resilience, said fibrous web comprising a plurality of openings extending therethrough in a direction of a thickness of the fibrous web, and barriers surrounding and defining said openings, said barriers comprising a shape holding layer formed from a plurality of thermoplastic synthetic resin fibers that are hot welded together at contact points between the thermoplastic synthetic resin fibers so as to resist collapsing under pressure and a body fluid retaining layer placed upon one of an upper surface and a lower surface of said shape holding layer and formed from a plurality of thermoplastic synthetic resin fibers which are mixed with an absorbent material and are hot welded together at contact points between the thermoplastic synthetic resin fibers so as to resist collapsing under pressure, said shape holding layer surrounding peripheral edges of each of the plurality of openings, said thermoplastic synthetic resin fibers of said shape holding layer being hot welded together at contact points thereof in said shape holding layer, said thermoplastic synthetic resin fibers of said body fluid retaining layer being hot welded together at contact points thereof in said body fluid retaining layer, and said thermoplastic synthetic resin fibers of said shape holding layer and said thermoplastic synthetic resin fibers of said body fluid retaining layer being hot welded to each other along an interface at contact points of said shape holding layer and said body fluid retaining layer.

* * * * *